Figure 1:
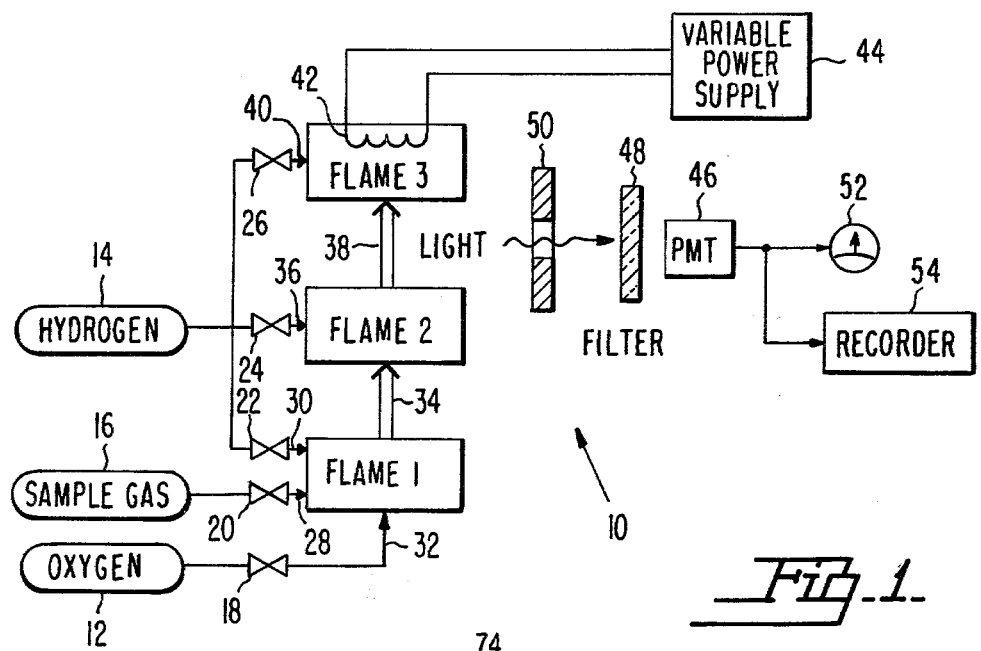

United States Patent [19]

Carter et al.

[11] 4,234,257
[45] Nov. 18, 1980

[54] FLAME PHOTOMETRIC DETECTOR ADAPTED FOR USE IN HYDROCARBON STREAMS

[75] Inventors: Harold V. Carter; Frederick G. Durfee, both of Falls Township, Bucks County, Pa.

[73] Assignee: Process Analyzers, Inc., Fallsington, Pa.

[21] Appl. No.: 3,101

[22] Filed: Jan. 15, 1979

[51] Int. Cl.³ .............................................. G01J 3/48
[52] U.S. Cl. .................................. 356/417; 250/554; 431/268
[58] Field of Search ............................... 356/417–419; 250/554; 422/54; 431/268; 431/329, 328

[56] References Cited
U.S. PATENT DOCUMENTS

| | | | |
|---|---|---|---|
| 3,245,459 | 4/1966 | Keith | 431/329 |
| 3,489,498 | 1/1970 | Brody et al. | 356/417 |
| 4,097,239 | 1/1978 | Patterson | 356/417 |

OTHER PUBLICATIONS

"Detectors in Gas Chromatography" by Jiri Sevcik, Amer. Elsevier, Pub. Co., Inc., N.Y. 1975, pp. 145–164.
A New Concept of Flame Photometric Detection of GC Effluents" by P. Paterson, R. Howe, U. Hornung, and Ahmad Abu-Shumays, Varian Inst. Div.

Primary Examiner—John K. Corbin
Assistant Examiner—Bruce Y. Arnold
Attorney, Agent, or Firm—Sanford J. Asman

[57] ABSTRACT

Gas analysis, intended primarily for the quantitative and qualitative analysis of sulfur, is performed utilizing flame photometry by burning a sample of the gas to be analyzed in a hydrogen rich flame in which combustion is supported by an excess of oxygen. A second hydrogen rich flame is used to reduce any sulfur present. A third flame is used to establish a thermal gradient which is particularly suited for the observation of the wavelengths emitted by sulfur. The actual detection of light emissions is accomplished using an appropriate filter and a photomultiplier tube. The detector of the present invention utilizes platinum flame holders in the first two flames and a platinum filament to induce the third flame and establish the aforementioned thermal gradient. A fourth platinum flame holder, preferably in the form of a mesh, is used to prevent flickering of the burning effluent gases which leave the detector, thereby reducing the noise level.

22 Claims, 2 Drawing Figures

FLAME PHOTOMETRIC DETECTOR ADAPTED FOR USE IN HYDROCARBON STREAMS

The present invention relates to a flame photometric detector and is particularly related to a flame photometric detector adapted to detect sulfur in a hydrocarbon stream.

Heretofore, flame photometric detectors have been used for the detection of sulfur and phosphorus compounds in gas streams. Such detectors have not been successfully used for the detection of sulfur or phosphorus when those elements are present in a hydrocarbon sample gas. In view of the fact that the presence of sulfur is extremely detrimental to many processes which employ hydrocarbon streams, such as processes which utilize a nickel catalyst, the ability to detect and measure the sulfur content of a hydrocarbon stream is extremely important. Accordingly, hereafter all reference will be limited to sulfur. However, such reference to sulfur should be construed to include other elements, such as phosphorus, or compounds thereof.

Flame photometric detectors used for the detection of sulfur operate by measuring the intensity of light emitted at a particular wavelength in response to energy added to excite the sulfur molecules. The excited molecules return to their ground state via either emission of radiative energy or by non-radiative de-excitation with another substance, such as by the so-called "quenching" reaction.

By monitoring appropriate wavelengths, representative of the emission characteristics of the element being investigated, the presence of that element can be determined qualitatively. Through the use of known calibration references, the flame photometric detector can be calibrated to provide accurate quantitative analysis.

Sulfur in the $S_2$ molecule exhibits a strong emission at 384 nm (3840 Å) and at 394 nm (3940 Å). Problems which have heretofore inhibited accurate detection of sulfur include the light output from interfering groups, i.e. light output having a strong emission at a wavelength close to that of sulfur, and the "quenching" reaction previously mentioned. In particular, the CN group has an emission peak at 385 nm. Accordingly, the detection of sulfur is particularly difficult when the combustion products of the sample gas include members of the CN group. Such gases as cyanogen ($C_2N_2$) are produced when hydrocarbons are burned in air, which is rich in nitrogen ($N_2$). While the CN groups can be eliminated by using oxygen rather than air to support combustion, thereby eliminating nitrogen from the stream, the presence of the C—H groups in hydrocarbon streams have also hampered efforts to use flame photometry for the detection of sulfur in hydrocarbon streams, because the C—H groups have strong emission peaks at 388.3 nm and at 390 nm.

In view of the spectral interference of hydrocarbons in the immediate vicinity of the sulfur emission, flame photometry could not heretofore be accurately employed with hydrocarbon streams unless the hydrocarbon was first separated by a gas chromatograph.

In addition, the "quenching" reaction, which is a non-radiative de-excitation process, significantly affects the detection mechanism in the flame photometric detector. The "quenching" phenomenon reportedly results from molecules of organic substances absorbing the energy of excited molecules, resulting in a simultaneous change in their vibrational and rotational states. The emission from the excited molecules decreases exponentially with increases in the concentration of the organic substance. Hydrocarbons substantially decrease the emission of sulfur.

Many of the problems discussed herein regarding the difficulty of detecting sulfur in hydrocarbon streams are more fully discussed in "Detectors in Gas Chromatography" by Jiri Sevcik, American Elsevier Publishing Company, Inc., New York (1975), pages 145–164, which book is incorporated herein by reference.

The present invention provides an improved flame photometric detector for detecting the presence of sulfur in a sample gas, which may be a hydrocarbon. In order to accomplish that result the flame photometric detector of the present invention employs three flames. The first flame is used to oxidize the sample gas in a hydrogen rich environment. The first flame is intended to fully burn any hydrocarbon present and to oxidize any sulfur which is present in the sample gas. A lean, i.e. an oxygen rich, mixture is preferably used to accomplish that result.

The second flame is used to reduce any sulfur present in order that the sulfur goes into the $S_2$ state wherein it will emit light having a wavelength of 394 nm. Accordingly, the second flame is rich in hydrogen, which gas serves as a reducing agent.

Devices having two flames of the type described above have heretofore been known, and one such device is shown in U.S. Pat. No. 3,489,498 issued to S. S. Brody et al. on Jan. 13, 1970. The present invention differs from such prior devices in that it includes means for containing the first two flames. In the preferred embodiment of the present invention, the means for containing the flames comprises platinum (Pt) wires which act as flame holders. In addition, platinum acts as a catalyst in a substantially stoichiometric mixture of hydrogen and oxygen, to self-ignite the mixture thereby eliminating the need to provide additional means for igniting the mixture. Thus, the platinum flame holders simultaneously act as ignitors and flame holders for accurately locating the flames and preventing them from flickering. Accordingly, the flame photometric detector of the present invention does not experience any flameout problems of the type heretofore experienced in the detectors of the prior art.

In addition to the platinum flame holders, the present invention employs a helical platinum filament located over the second flame. The platinum filament, which has not heretofore been employed in flame photometric detectors is heated by passing an electrical current therethrough in order to produce the third flame. The third flame is comprised of the remaining combustible materials which are present in the gas flow. The inventors believe that a temperature gradient exists between the second and third flames which can be adjusted by correctly setting the gas flow rates and the current through the helical platinum filament. They believe that the thermal gradient provides optimal conditions for observing the sulfur emission.

Each of the three flames described is located within a glass chimney which in turn is located within a light tight box. As a result of the combined elements described herein, the present invention provides a flame photometric detector which is much more sensitive to sulfur in hydrocarbon streams than any detectors heretofore known.

IN THE DRAWINGS

Figure 2:
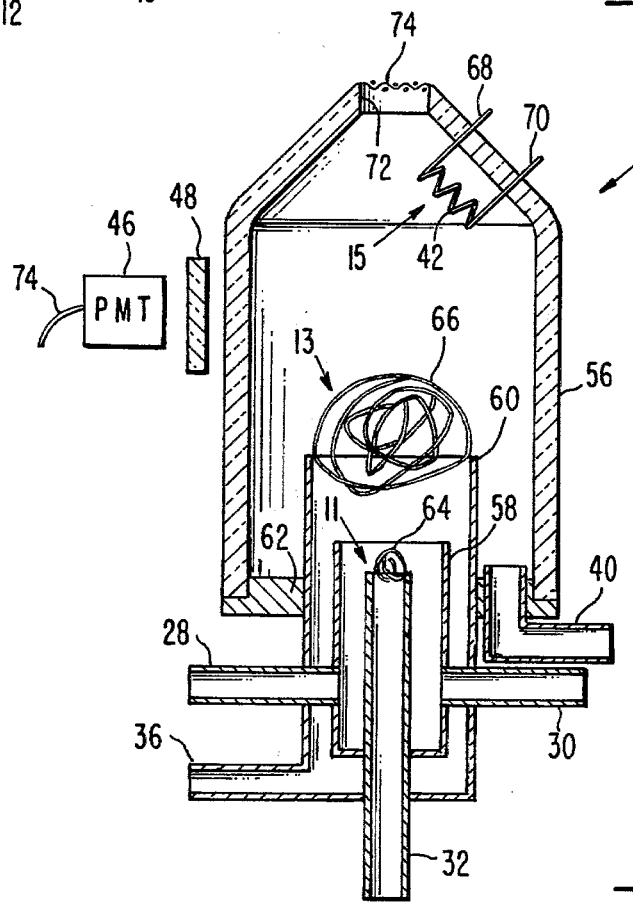

FIG. 1 is a diagrammatic illustration of the flame photometric detector of the present invention; and FIG. 2 is a cross-sectional view of the flame photometric detector.

Referring now to FIG. 1, the flame photometric detector 10 of the present invention is shown diagrammatically. The detector 10 comprises supplies of oxygen gas 12, hydrogen gas 14, and a sample gas 16, which sample gas may comprise a hydrocarbon containing an unknown amount of sulfur. A valve 18 controls the flow rate of oxygen, and a valve 20 controls the flow rate of the sample gas. In the preferred embodiment in the invention three valves 22, 24, 26 are used to control the flow rate of hydrogen.

In the operation of the detector 10, the sample gas flows from its supply 16 through a line 28, with its flow rate controlled by valve 20. Similarly, hydrogen flows from its supply 14 through a line 30, with its flow rate controlled by valve 22, and oxygen flows from its supply 12 through a line 32, with its flow rate controlled by a valve 18. The hydrogen flowing through line 30 combines with the sample gas flowing through line 28 and oxygen flowing through line 32 to produce Flame 1. In the preferred embodiment of the invention, the valves 18, 20, 22 are adjusted to provide a sample gas flow rate through line 28 on the order of 1 ml/min., a hydrogen gas flow rate through line 30 of between about 2 and 5 ml/min. and an oxygen flow rate through line 32 suitable to provide an oxygen rich but substantially stoichiometric mix at Flame 1. Flame 1 is intended to fully burn the sample gas and to oxidize any sulfur present in the sample gas.

The combustion products of Flame 1 (represented by the double arrow 34) flow upward through the detector 10 and are combined with additional hydrogen provided through a line 36, whose flow rate is controlled by valve 24, to produce Flame 2. The flow rate of the hydrogen through line 36 is adjusted so that Flame 2 is hydrogen rich. Flame 2 thus provides a reducing atmosphere capable of producing sulfur gas ($S_2$) in the combustion products of Flame 2 (represented by the double arrow 38) if sulfur was present in the sample gas.

The combustion products 38 of Flame 2 flow upward through the detector 10 and are combined with additional hydrogen provided through line 40, whose flow rate is controlled by valve 26, to produce Flame 3. Flame 3 is produced at an electrically heated platinum filament 42 which acts both as a heater and as a catalyst to self-ignite Flame 3. The Platinum filament 42 is helical in form and has a voltage imposed across it by means of a variable power supply 44 which can be adjusted to alter the amount of heat produced electrically at the filament 42. In the preferred embodiment of the invention, a variable transformer is used to supply about 6 volts a.c. to the filament 42. A variable d.c. supply can also be used, and a d.c. supply may provide the detector 10 with greater noise immunity.

In the operation of the detector 10, a photomultiplier tube 46 is used to examine the light emissions in the combustion products 38 of Flame 2 as they rise upward in the detector toward Flame 3. The photomultiplier tube 46 views the combustion products 38 of Flame 2 through a band pass filter 48 which is selected to substantially eliminate light outside the particular region of sulfur emission.

In the preferred embodiment of the invention, the filter 48 has a peak transmission centered at about 394 nm (3940 Å). The pass band of the filter 48 lies between about 389 nm and 399 nm. Thus, the filter 48 is intended to prevent the photomultiplier tube 46 from receiving light other than light which is emitted by sulfur. It is preferable to include shields 50 in the detector 10 to shield the photomultiplier tube 46 from light given off directly by either Flame 2 or by Flame 3. The output of the photomultiplier tube 46 is preferably fed to a meter 52 and a permanent record is made on a suitable chart recorder 54.

Referring now to FIG. 2, a cross-sectional view of the flame photometric detector 10 of the present invention is shown. The detector 10 comprises a silica glass envelope or chimney 56 which is open at the top and closed by a base 62 at the bottom. In the preferred embodiment of the invention the base 62 is made of stainless steel. The burners 11, 13, 15 which contain Flame 1, Flame 2, and Flame 3, respectively, are housed within the glass chimney 56. Entering the chimney 56 through the base 62 is an oxygen line 32 which is comprised of a stainless steel tube having a 1/16 inch outside diameter in the preferred embodiment of the invention. A second stainless steel tube 58 having an outside diameter of ⅛ inch in the preferred embodiment of the invention surrounds the oxygen line 32 and is concentric therewith. The sample gas line 28 and the hydrogen line 30 open into the ⅛ inch diameter tube 58. Those lines 28, 30 enter the second tube 58 after passing through the walls of a third concentric stainless steel tube 60. In the preferred embodiment of the invention, the third stainless steel tube 60 has an outside diameter of approximately ¼ inch. While appropriate seals and fittings are required where the various tubes pass through one another and where the base 62 joins the chimney 56, such seals and fittings would be obvious to those skilled in the art. Accordingly, they are not shown in the drawing.

The hydrogen line 36 enters and opens into the third tube 60. Finally, the hydrogen line 40 enters the chimney 56 through its base 62, and that line 40 opens into the chimney 56.

A platinum wire 64 is formed across the top of the oxygen line 32 and acts as a flame holder for Flame 1 as has been heretofore described. The flame holder 64 contains Flame 1 which is formed when oxygen entering the second tube 58 through line 32 combines at the first burner 11 with sample gas flowing through line 28 and hydrogen flowing through line 30. The presence of the platinum flame holder 64 insures that Flame 1 will self-ignite at the burner 11 when the proper gas ratios are present. The flame holder 64 also insures that Flame 1 will not flicker and that it will be accurately located.

Similarly, a ball of platinum wire acts as a flame holder 66 at the second burner 13 located at the mouth of the third stainless steel tube 60. As previously discussed, the platinum flame holder 66 acts to contain Flame 2 and as a self-igniter of Flame 2. Flame 2 is formed by the combination of hydrogen gas entering the third tube 60 through the hydrogen line 36 and combining with the combustion products 34 (shown in FIG. 1) leaving the first burner 11. As previously discussed, the flow rates of the gases entering the second burner 13 are adjusted so that Flame 2 is hydrogen rich. The hydrogen rich combustion of Flame 2 reduces sulfur from the compounds (predominately $SO_2$) present in the combustion products 34 of Flame 1.

Additional hydrogen enters the chimney 56 through line 40 which extends through the base 62 and opens into the chimney. Such additional hydrogen flows upward through the chimney 56 where it is burned at Flame 3 which is formed around the platinum filament 42 located at the top of the chimney 56. Electrical wires 68, 70 extend from the filament 42 through the side wall of the chimney 56 through appropriate seals (not shown). The wires 68, 70 are electrically connected to an appropriate power supply such as the variable transformer 44 used in the preferred embodiment of the invention.

Finally, any remaining gases which are not burned in Flame 3 at the third burner 15 are burned in air as they exit the mouth 72 of the chimney 56. A platinum flame holder 74 is used at the mouth 72 of the chimney 56. Preferably, the flame holder 74 is in the form of a mesh at the mouth 72 of the chimney 56, so that it acts as a self-ignitor.

The filter 48 and the photomultiplier tube 46 previously discussed (with reference to FIG. 1) are shown adjacent the side wall of the chimney 56. They are located between the second and third burners 13, 15. The shields 50, shown in FIG. 1, may be included if desired in order to block light eminating from either Flame 2 or Flame 3 from the view of the photomultiplier tube 46 through the filter 48. A bundle of leads 74 extends from the photomultiplier tube 46. The leads are used to connect the photomultiplier tube 46 to an appropriate power supply (not shown) and to the meter 52 and chart recorder 54 shown in FIG. 1.

In the preferred embodiment of the invention, the detector 10 also includes the valves 18, 20, 22, 24, 26 heretofore discussed with reference to FIG. 1 together with appropriate flow meters for determining the flow rates of the various gases. These valves and flow meters are standard items which are not shown in FIG. 2. The detector 10 is preferably housed in a light tight box (not shown) designed to prevent ambient light from reaching the photomultiplier tube 46.

In order to operate the detector 10, hydrogen gas is first flowed from the hydrogen supply 14 through line 40 at about 20–40 ml/min. in order to purge gases from the chimney 56. Next, the hydrogen flow through the line 30 is started and increased until the hydrogen flow rate through line 30 is between about 2 and 5 ml/min. Thereafter, the flow of oxygen from the oxygen supply 12 through line 32 is started and the oxygen flow rate is increased by adjusting the valve 18 until there is combustion at both the first and second burners 11, 13. Flame 1, located at flame holder 64, and Flame 2, located at flame holder 66, will both self-ignite due to the catalytic action of the platinum wire 64 and the platinum flame holder 66. Excess hydrogen flowing through the chimney 56 will begin to burn in air at the mouth 72 of the chimney 56.

Next, the flow of the sample gas into the first burner 11 through line 28, is started. The sample gas flow rate is adjusted to about 1 ml/min. by using valve 20. Finally, additional hydrogen gas is admitted through line 36 by opening valve 24.

The flow rates of hydrogen through the various hydrogen lines 30, 36, 40 and the flow rate of oxygen through line 32 are tuned by adjusting the valves 22, 24, 26, 18, respectively, to obtain a substantially stoichiometric mix at the platinum filament 42 in order to have both catalytic combustion and electric heat induced combustion at the filament 42. In addition, the voltage across the platinum coil 42 is tuned by making appropriate adjustments to the variable transformer 44 (shown in FIG. 1).

When the various gas flow rates and the electrical voltage have been properly tuned, the detector 10 is extremely sensitive to the presence of sulfur products. Its sensitivity is approximately 100 times greater than any similar detectors heretofore known. The inventors believe that the great sensitivity of the detector 10 of the present invention is attributable to the accurate location of Flame 1 and Flame 2 and avoidance of flicker of those flames, together with the thermal gradient produced between Flame 2, located at flame holder 66, and Flame 3 located at the platinum coil 42. The accurate location of Flame 1 and the avoidance of flicker of Flame 1 are attributed to the platinum flame holder 64. Similarly, the accurate location of Flame 2 and the avoidance of flicker of Flame 2 is attributed to the platinum flame holder 66.

The inventors believe that the thermal gradient produced between Flame 2 and Flame 3 provides an optimal viewing region for observing the spectral emission of sulfur ($S_2$) at the 394 nm wavelength. The thermal gradient is attributable to the use of the third burner comprised of the platinum filament 42. Finally, the noise level is kept low by using the flame holder 74 at the mouth 72 of the chimney 56 to prevent flickering of the flame resulting from the combustion in air of the effluent gases. The burning of the effluent gases is thought to prevent nitrogen from entering the chimney 56 while also keeping the temperature substantially constant at the mouth 72 of the chimney 56. Accordingly, the particular structure of the flame photometric detector 10 represents a number of improved features which act together to provide an extremely sensitive detector for sulfur, even when the sample gas is a hydrocarbon.

As has been previously discussed, the detector 10 is not limited to use with hydrocarbon samples. Nor is it limited to the detection of sulfur. By using an appropriate filter and by making adjustments to the valves and to the power supply, other elements may be detected.

While the description of the present invention has referred to "Flame 3" it should be understood that the "flame" adjacent the platinum filament 42 is not of the type normally thought of. In particular "Flame 3" is the term used to refer to the area adjacent the platinum filament 42 where oxidation of gases is catalytically supported by the heated filament 42.

It should also be recognized that while a photomultiplier tube 46 has been used in the preferred embodiment of the invention, any suitable photodetector means can be employed in place of a photomultiplier tube. Accordingly, the term "photomultiplier tube" as used herein should be construed to mean any photodetector responsive to light of a selected wavelength, which wavelength is characteristic of the presence of the particular element which is being detected.

As has heretofore been discussed, it is expected that the primary use of the present invention will be for the detection of sulfur. However, the detector 10 may also be used for the detection of phosphorus. In order to use the detector 10 for the detection of phosphorus, the photomultiplier tube 46 will have to be one which is sensitive to a wavelength emitted by phosphorus and the filter 48 will have to have a pass band appropriate for the detection of light emitted by phosphorus. A particular wavelength which would be appropriate for detecting phosphorus is 526 nm.

Finally, the filter 48 can be any suitable type of pass band filter. However, in the preferred embodiment of the invention an interference filter is used.

We claim:

1. An improved flame photometric detector of the type comprising:
   (a) a first burner;
   (b) means for supplying to said first burner a sample gas, hydrogen, and oxygen;
   (c) a first flame holder extending into said first burner, said first flame holder being adapted to act as an ignition means for said first burner and for locating a first flame therein;
   (d) a second burner surrounding said first burner, said second burner including means for combining additional hydrogen gas with the combustion products of said first flame;
   (e) a second flame holder extending into said second burner, said second flame holder being adapted to act as an ignition means for said second burner and for locating a second flame therein; and
   (f) photodetector means for examining the light emissions in the combustion products of said second flame, said photodetector means being responsive to a given wavelength of light emitted by said second flame, said given wavelength of light being characteristic of the presence of the element being detected;

wherein the improvement comprises a third burner located in the stream of combustion products from said second flame, said third burner comprising:
   (a) means for combining additional hydrogen gas with the combustion products of said second flame;
   (b) an electrically heated filament which also acts as a catalyst for oxidizing gases adjacent said filament; and
   (c) means for supplying a current through said filament.

2. The flame photometric detector of claim 1 wherein at least one of said flame holders is made of platinum.

3. The flame photometric detector of claim 2 wherein said photodetector comprises a photomultiplier tube.

4. The flame photometric detector of claim 2 further comprising an optical band pass filter in the optical path between said photodetector and the combustion products of said second flame, the pass band of said filter being substantially limited to a wavelength of light characteristic of the element being detected.

5. The flame photometric detector of claim 4 wherein the pass band of said filter is substantially centered around 394 nm, and the element being detected is sulfur.

6. The flame photometric detector of claim 4 wherein the pass band of said filter is substantially centered around 526 nm and the element being detected is phosphorus.

7. The flame photometric detector of claim 4 wherein said band pass filter is comprised of an interference filter.

8. The flame photometric detector of claim 1 wherein each of said flame holders is made of platinum.

9. The flame photometric detector of claim 1 wherein said filament is formed of platinum.

10. The flame photometric detector of claim 9 further comprising means for regulating the flow rates of the gases entering said first, second, and third burners.

11. The flame photometric detector of claim 10 wherein said photodetector is adapted to respond to the light emissions in the combustion products lying between said second flame and said filament.

12. The flame photometric detector of claim 11 further comprising means for shielding from said photodetector that portion of said second flame which is held by said second flame holder.

13. The flame photometric detector of claim 11 further comprising means for shielding the photodetector from said filament.

14. The flame photometric detector of claim 1 wherein said means for supplying current comprises a variable power supply.

15. The flame photometric detector of claim 1 further comprising a glass chimney surrounding said first, second, and third burners and separating them from said photodetector, said glass chimney being substantially cylindrical and having an opening at its top and having a base which closes off its bottom, said first and second burners and the means for supplying gases thereto extending through said base.

16. The flame photometric detector of claim 15 wherein said glass chimney is comprised of a silica glass.

17. The flame photometric detector of claim 15 wherein said base is comprised of stainless steel.

18. The flame photometric detector of claim 15 further comprising a fourth flame holder at the opening in the top of said chimney, said flame holder adapted to prevent the flickering of effluent gases which oxidize in air upon leaving said chimney.

19. The flame photometric detector of claim 18 wherein said fourth flame holder is comprised of a wire mesh which covers said opening in said chimney.

20. The flame photometric detector of claim 19 wherein said wire mesh is comprised of platinum.

21. The flame photometric detector of claim 1 further comprising a light tight box which encloses the other elements of said detector.

22. The flame photometric detector of claim 1 wherein said first burner, said second burner, and said means for supplying gases thereto are constructed of stainless steel.

* * * * *